United States Patent [19]
Flanders

[11] Patent Number: 5,344,450
[45] Date of Patent: Sep. 6, 1994

[54] REPAIR KIT FOR EXTERNALLY WORN SILICONE BREAST PROSTHESIS

[76] Inventor: Nancy L. Flanders, P.O. Box 45, Cold River Rd., North Clarendon, Vt. 05759

[21] Appl. No.: 51,231

[22] Filed: Apr. 23, 1993

Related U.S. Application Data

[63] Continuation of Ser. No. 814,812, Dec. 31, 1991, abandoned.

[51] Int. Cl.$^5$ .............................................. A61F 2/52
[52] U.S. Cl. ...................................................... 623/7
[58] Field of Search ............... 623/8, 7; 128/DIG. 21; 202/339, 803, 813

[56] References Cited

U.S. PATENT DOCUMENTS

| | | | |
|---|---|---|---|
| 591,501 | 10/1897 | Schonborn | 152/367 |
| 1,643,926 | 9/1927 | Dickson | 602/41 |
| 2,096,389 | 10/1937 | Bode | 206/813 |
| 2,278,673 | 4/1942 | Savada et al. | 206/813 |
| 2,346,219 | 4/1944 | Johnson | 206/813 |
| 2,547,487 | 4/1951 | Penney | 152/367 |
| 3,402,716 | 1/1964 | Baxter . | |
| 4,143,767 | 3/1979 | MacDonald | 152/367 |
| 4,394,904 | 7/1983 | Larimore | 206/813 |
| 4,570,627 | 11/1986 | MacConkey et al. . | |
| 4,666,040 | 9/1987 | Murata . | |
| 4,773,909 | 9/1988 | Chaglassian | 623/8 |
| 4,787,380 | 10/1988 | Scott . | |
| 4,829,995 | 4/1989 | Metters . | |
| 4,938,414 | 7/1990 | Lippert | 206/813 |
| 4,966,138 | 10/1990 | Chow et al. | 602/57 |
| 5,104,409 | 4/1992 | Baker | 623/8 |

FOREIGN PATENT DOCUMENTS

| | | | |
|---|---|---|---|
| 1323319 | 7/1970 | United Kingdom | 128/155 |

Primary Examiner—David Isabella
Attorney, Agent, or Firm—Richard C. Litman

[57] ABSTRACT

A kit for the repair of damaged prosthetic devices provides for the expeditious and economical repair of such prostheses. The kit is directed primarily to the repair of externally worn silicone gel filled breast prostheses, which prostheses are relatively costly and perhaps more vulnerable to damage than other types. The basic member of the kit is a thin, flexible adhesive backed tape of vinyl or other suitable material, which tape may be stored on a backing sheet. The backing sheets may be in the form of a roll, or alternatively several planar sheets may be included in a relatively flat container for persons who may not be able to conveniently carry a bulky roll. Several shapes and sizes of tapes may be included in a single kit, and different kits may include different coloring, shading and/or texture in order that the user may most closely approximate the proper coloring, shading and/or texture of the damaged prosthesis. However, each of the repair tapes in a given kit are of like coloring, shading and texture in order that all repair tapes in that given kit will closely approximate the coloring, shading and/or texture of the prosthesis for which the repair kit was made.

6 Claims, 1 Drawing Sheet

REPAIR KIT FOR EXTERNALLY WORN SILICONE BREAST PROSTHESIS

CROSS-REFERENCE TO RELATED APPLICATION

This is a continuation of Ser. No. 07/814,812 filed Dec. 31, 1991 abandoned.

FIELD OF THE INVENTION

This invention relates generally to adhesive materials used for the repair of various articles, and more specifically to a repair kit comprising a variety of shapes, sizes and colors of adhesive patches for the expeditious mending or repair of externally worn silicone breast prostheses.

BACKGROUND OF THE INVENTION

Diseases and accidents which disfigure the body are occurrences which are unfortunately all too frequent. In times past, many of these diseases and accidents proved fatal, but modern medicine has seen tremendous strides made in the recovery of victims of such accidents and/or diseases. However, there remains the problem of the resulting disfigurement, which most persons wish to correct in some way.

All persons are concerned with their physical appearance, at least to a certain extent, and various prosthetic devices have been developed in order to afford afflicted persons an essentially normal appearance. One group of people who have been particularly affected by the disfigurement resulting from disease, is women who have been so unfortunate as to incur breast cancer. The radical medical cure is the removal of one or both breasts and often much of the surrounding tissue, which procedure obviously results in severe disfigurement. The resulting disfigurement is even more unfortunate than in times past, due to modern clothing styles which tend to be lighter and more revealing than in generations past.

To overcome such breast disfigurement, various breast prostheses have been developed which may be worn beneath a woman's clothing adjacent to the body. The most realistic of these prostheses are formed of a relatively viscous silicone gel, which gel is contained in an appropriately shaped and colored enclosure which serves to simulate a human female breast. These prostheses provide many advantages over other types, in that the silicone gel is approximately the same density as the fatty tissues of the normal human female breast, and the relatively viscous nature of the silicone gel provides a texture and resilience closely approximating that of a normal human female breast. Other padded or otherwise constructed breast prostheses fail to achieve such realism.

As with most articles which provide advances over the prior art, such silicone filled breast prostheses are also prone to various disadvantages. They are relatively costly in comparison to other less realistic types, and in some ways they are more susceptible to damage. Nevertheless, they have proven very popular with thousands of women due to their realism. However, a small tear or puncture of the outer containment vessel of the prosthesis may be fatal to the device, due to the fluid nature of the silicone gel used to fill the prosthesis. While many women have temporarily repaired such damaged silicon prostheses with an adhesive tape of some form, the results are far from satisfactory due to the general wide variation in texture and color between the tape and the surface of the prosthesis. Some might consider the use of an adhesive bandage as a repair, but the nature of the gauze or other padding of the bandage renders it unsatisfactory for such repairs as the silicone gel may leak from the area of the bandage pad. Moreover, the relative thickness of the bandage pad produces an unsightly lump at the point of application.

The need arises for a kit or system for the repair of externally worn silicone breast prostheses. The repair apparatus should provide a relatively thin and flexible plastic sheet which will not produce any unevenness or bulges at the place of application, and should provide for a variety of flesh tones or colors in order that a close match may be made. The repair must be capable of being quickly and easily applied, and such a kit should be relatively thin and lightweight in order that a woman may easily carry it in her pocket without undue annoyance due to excessive bulk. The kit should also contain a variety of various sizes and shapes of adhesive patches, in order that a reasonably suitably sized and shaped patch may be selected for a given damaged area of the prosthesis.

DESCRIPTION OF THE RELATED ART

T. R. Baxter U.S. Pat. No. 3,402,716 issued Sep. 24, 1968 discloses an Adhesive Strip Suture for the repair of relatively small wounds to the body. As such, requirements for packaging and sterility are incorporated which extend beyond the scope of the present invention. Moreover, the protective material provided is unlike that of the present invention.

J. S. MacConkey et al. U.S. Pat. No. 4,570,627 issued Feb. 18, 1986 discloses a Membrane Dispensing Assembly And Method Of Manufacture. The membrane is vapor permeable, unlike that of the present invention, due to its use as a means of closing wounds. Moreover, the apparatus of this patent is not directed to the repair of inanimate prostheses, as is the present invention.

T. Murata U.S. Pat. No. 4,666,040 issued May 19, 1987 discloses a Small Article Holding Package directed to adhesive bandages and the like. The present invention is not a bandage, and moreover the packaging provided with the present invention is a considerable improvement over the prior art and the cumbersome dispensing means provided thereby.

D. F. Scott U.S. Pat. No. 4,787,380 issued Nov. 29, 1988 discloses a Delivery System And Package For A Self Adhering Polymer Medical Dressing. This device is directed to an adhesive sheet providing a medical dressing, which renders it unsuitable for use in the field of the present invention as discussed above.

J. R. Metters U.S. Pat. No. 4,829,995 issued May 16, 1989 discloses a Fluid Barrier For Medical Dressing. The device provides a handle means permitting it to be applied to a dressing, which assembly may then be applied to a wound. The barrier is then removed, unlike the present invention.

None of the above noted patents, either singly or in combination, are seen to disclose the specific arrangement of concepts disclosed by the present invention.

SUMMARY OF THE INVENTION

By the present invention, an improved means for the repair of human prosthetic devices, particularly externally worn silicon filled breast prostheses, is disclosed.

Accordingly, one of the objects of the present invention is to provide an improved repair kit for the mending of such prosthetic devices.

Another of the objects of the present invention is to provide a variety of self adhering repair tapes, which repair tapes may be varied by size, shape and color in order to more closely conform to the damaged area and shading of the prosthetic device.

Yet another of the objects of the present invention is to provide repair tapes of relatively thin and flexible material, in order to preclude unsightly variations in the contour of the prosthetic device after the tape has been applied.

Still another of the objects of the present invention is to provide a for repair to such prostheses which is relatively quick, easy to accomplish and inexpensive.

A further object of the present invention is to provide for a repair kit for such prosthetic devices which kit may be easily carried in a pocket or purse without undue bulk, and yet still provides for a variety of repair tapes.

An additional object of the present invention is to provide a repair for such prosthetic devices which repair requires no special equipment to accomplish and which may be accomplished rapidly after damage has occurred.

With these and other objects in view which will more readily appear as the nature of the invention is better understood, the invention consists in the novel combination and arrangement of parts hereinafter more fully described, illustrated and claimed with reference being made to the attached drawings.

BRIEF DESCRIPTION OF THE DRAWINGS

Similar reference characters designate corresponding parts throughout the several figures of the drawings.

DESCRIPTION OF THE PREFERRED EMBODIMENT

Figure 2:
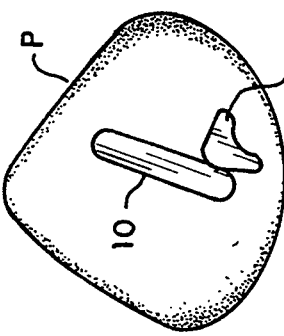
FIG. 2 is a front perspective view of the prosthesis of FIG. 1, showing a plurality of at least partially overlapping repair tapes applied.
Figure 1:
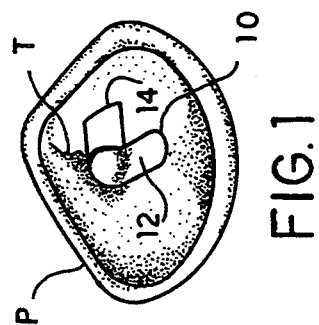
FIG. 1 is a rear perspective view of an externally worn silicone breast prosthesis showing a damaged area and a repair tape of the present invention being applied.

Referring now to the drawings, particularly FIGS. 1 and 2 of the drawings, the present invention will be seen to relate to an adhesive tape means for the expeditious and convenient repair of damage which has been incurred by a prosthesis, particularly an externally worn silicone gel breast prosthesis. Repair tape 10 of FIG. 1 will be seen to comprise a thin, flexible sheet of material having an outer surface 12 and inner surface 14. Inner surface 14 is coated with an adhesive material which will adhere to materials such as the plastics and vinyls of which externally worn silicone gel filled breast prostheses P generally use for an outer containment vessel for the silicone gel. Tape 10 may be formed of a thin deformable vinyl or other plastic sheet material in order to better conform to the varying shapes, contours and compound curves of such prostheses P.

Outer surface 12 is colored and shaded to closely match the skin tone with which such prostheses P are generally made, and of course may be provided with a variety of colors and tones in order to provide a close approximation of a color match for a wide variety of such differently colored or shaded prostheses P.

Figure 4:
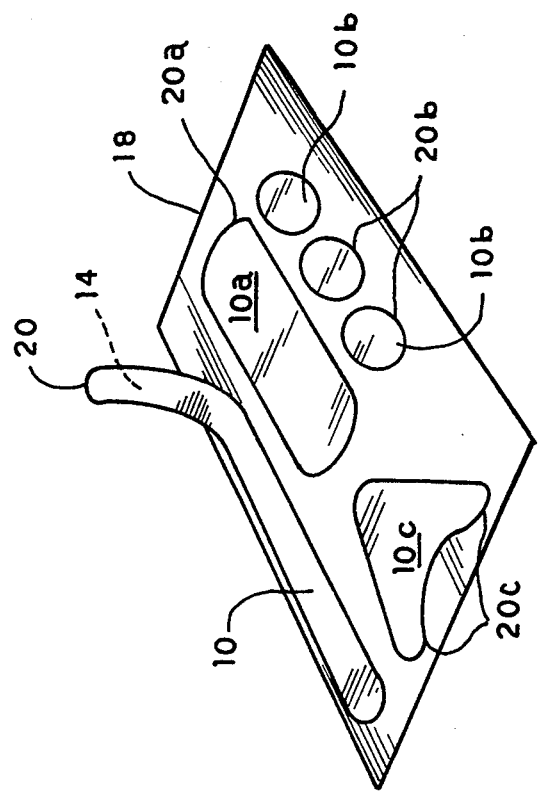
FIG. 4 is a perspective view of a plurality of various repair tapes and a common backing sheet.
Figure 5:
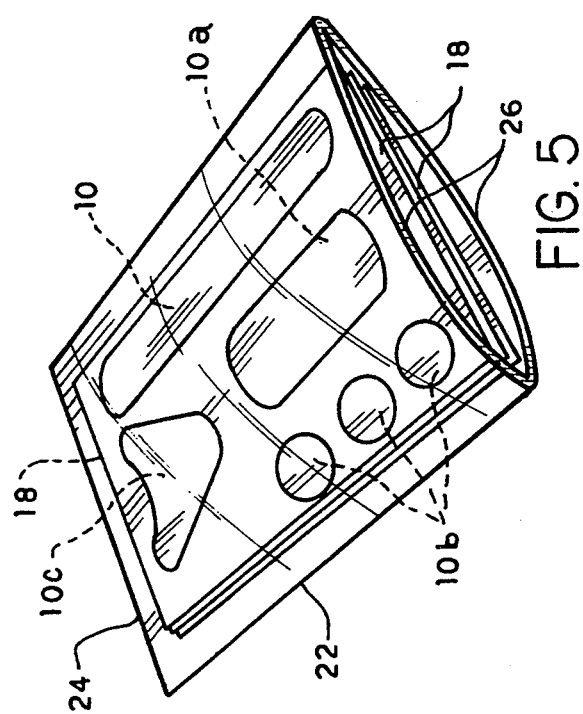
FIG. 5 is a perspective view of a compact container for a plurality of repair tape sheets as shown in FIG. 4.
Figure 3:
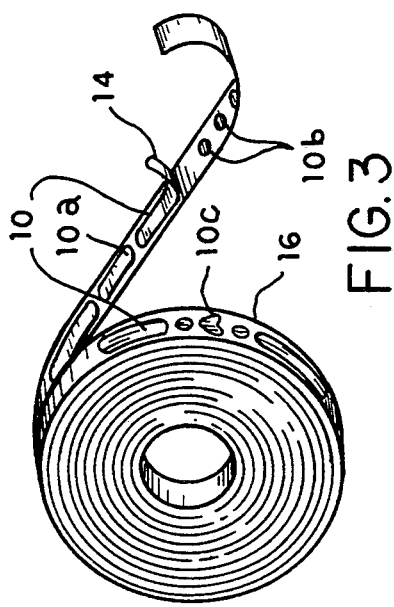
FIG. 3 is a perspective view of one means of containing or dispensing the repair tapes of the present invention and some of the various shapes and sizes of repair tapes possible.

Repair tapes may also be provided in a variety of different shapes and sizes, as may be seen in FIGS. 3 through 5. As such tapes are universally provided with an adhesive inner surface 14, they may be affixed to a roll of material 16 for dispensing, as shown in FIG. 3, or alternatively to a sheet of material 18 as shown in FIG. 4. Other storage or dispensing means are of course possible. Sheet 18 contains a plurality of various shapes and sizes of repair tapes, such as the elongated ovoid shape of tape 10, smaller ovoid shapes 10a, circular patches 10b, or irregular patches 10c. Preferably, all corners 20 through 20c of each of the shapes 10 through 10c are rounded in order to preclude the possibility of a sharp corner beginning to lift after application.

While it may be convenient to provide a plurality of prosthesis repair tapes 10 through 10c on a single linear backing sheet formed into a roll 16, for some persons, others needing such repair tapes 10 through 10c may not wish to carry such a relatively bulky roll 16 of tapes 10 through 10c upon their person. In any cases, a woman who may have need for such prosthesis repair tapes 10 through 10c may not be carrying a purse at the moment, and a means of providing a plurality of tapes 10 through 10c in a less bulky form would be highly desirable in order that such means might be conveniently carried in a pocket, for example. The kit 22 of FIG. 5 provides such means.

Kit 22 comprises a plurality of sheets 18, each of which contains a plurality of prosthesis repair tapes 10 through 10c which are in turn stored within a generally planar container 24. Container 24 may be sealed in order to maintain the cleanliness of sheets 18 and tapes 10 through 10c contained thereon, by means of a cooperating deformable and releasable seal 26 formed in one end of container 24. As tapes 10 through 10c are nominally only some few thousandths of an inch thick, or less, and the backing sheets 18 are of the same order of thickness, it will be seen that a stack of some five or six sheets 10 including tapes 10 through 10c will have a total thickness of on the order of 1/16th inch or less. Even when the added thickness of the sides of container 24 are included, as they are to complete a kit 22, the total thickness is still on the order of 1/10th inch or less. The relatively thin package provided may be easily carried in a pocket or otherwise without producing any undesirable bulk.

A cut or tear, designated as T in FIG. 1, may occur due to accidental contact with a hook or other fastener in clothing when a prosthesis P is being applied, or for any one of a number of other reasons. Should such a tear T occur, an appropriately sized and shaped repair tape 10 through 10c may be removed from the backing material of roll 16 or sheet 18, thereby exposing the underlying adhesive surface of inner surface 14. The damaged area or tear T may be held closed insofar as possible, and tape 10 through 10c applied for the repair. Due to the pliant nature of the relatively thin plastic material preferably used for the present invention, tape 10 through 10c will closely conform to the surface of prosthesis P as it is installed, thereby producing a repair which closely matches the original surface of prosthesis P.

In the event that a damaged area or tear exceeds the dimensions of any single repair tape 10 through 10c, a plurality of tapes may be applied, such as tapes 10c applied overlapping tape 10 shown in FIG. 2. Another circumstance which may lead to the plural application of repair tapes 10 through 10c, would be subsequent damage to a previously repaired prosthesis P. In any case, the versatility of such repair tapes 10 provides for the expedient and economical repair of such costly prostheses P.

It is to be understood that the present invention is not limited to the sole embodiment described above, but encompasses any and all embodiments within the scope of the following claims.

I claim:

1. A kit for repairing an externally worn breast prosthesis, comprising:
   an externally worn breast prosthesis, and;
   a plurality of differently configured repair tapes being formed of liquid impermeable material and including an outer surface closely approximating the flesh color, shading and texture of said externally worn breast prosthesis and an inner surface having an adhesive coating providing for the adhesive application of said repair tapes to said externally worn breast prosthesis to effect the repairs thereof, whereby
   a user of said externally worn breast prosthesis may make emergency repairs to said externally worn breast prosthesis, thereby substantially concealing the damage to said externally worn breast prosthesis with said one of said repair tapes substantially blending and conforming with said flesh color, shading and texture of said externally worn breast prosthesis when damage occurs thereto, without resorting to unsightly tapes, the kit being readily transportable by the user.

2. A kit as in claim 1, wherein:
   said plurality of differently configured repair tapes include at least one repair tape having an elongated ovoid shape, at least one repair tape having a circular shape, and at least one repair tape having an irregular shape, whereby
   a variety of differently shaped and sized tears damaging said externally worn prosthesis may be easily and conveniently repaired.

3. A kit as in claim 1, wherein:
   each of said plurality of differently configured repair tapes within each said kit is of like color, shading and texture,
   said like color, shading and texture closely approximating said externally worn breast prosthesis in flesh color, shading and texture.

4. The kit of claim 1 wherein:
   said externally worn breast prosthesis comprises an enclosure containing viscous silicone gel therein.

5. The kit of claim 1 including:
   a generally planar container having a resealable opening along one edge and sealed remaining edges;
   said container providing for the storage and containment of said at least one planar backing sheet having repair tapes thereon.

6. The kit of claim 1 further comprising:
   a rolled linear backing sheet having a plurality of differently configured repair tapes removably mounted thereon;
   said rolled linear backing sheet providing for the storage and containment of said plurality of repair tapes thereon.

* * * * *